(12) United States Patent
Wojciechowski et al.

(10) Patent No.: US 11,497,843 B2
(45) Date of Patent: Nov. 15, 2022

(54) NEGATIVE PRESSURE DEVICE INCLUDING EXPANDABLE SEGMENT

(71) Applicant: Aatru Medical, LLC, Cleveland, OH (US)

(72) Inventors: Timothy Wojciechowski, Westlake, OH (US); Richard L. Middaugh, Rocky River, OH (US); Thomas E. Lash, Chardon, OH (US); John Buan, Maple Grove, MN (US)

(73) Assignee: AATRU MEDICAL, LLC, Cleveland, OH (US)

( * ) Notice: Subject to any disclaimer, the term of this patent is extended or adjusted under 35 U.S.C. 154(b) by 0 days.

(21) Appl. No.: 17/283,396

(22) PCT Filed: Oct. 16, 2019

(86) PCT No.: PCT/US2019/056430
§ 371 (c)(1),
(2) Date: Apr. 7, 2021

(87) PCT Pub. No.: WO2020/106383
PCT Pub. Date: May 28, 2020

(65) Prior Publication Data
US 2021/0379274 A1 Dec. 9, 2021

Related U.S. Application Data (60) Provisional application No. 62/769,748, filed on Nov. 20, 2018.

(51) Int. Cl.
*A61M 1/00* (2006.01)
*A61F 13/02* (2006.01)

(52) U.S. Cl.
CPC ......... *A61M 1/964* (2021.05); *A61F 13/0216* (2013.01); *A61M 1/98* (2021.05)

(58) Field of Classification Search
CPC .......... A61M 1/964; A61M 1/98; A61M 1/80; A61M 1/82; A61M 1/90; A61M 1/74; A61F 13/0216; A61F 13/00068
See application file for complete search history.

(56) References Cited

U.S. PATENT DOCUMENTS 4,529,402 A * 7/1985 Weilbacher .......... A61M 1/0011
D24/111
8,460,255 B2 * 6/2013 Joshi ................... A61F 13/0216
602/42

(Continued)

FOREIGN PATENT DOCUMENTS

GB         2431351 A  *  4/2007  .......... A61M 1/0011
WO  WO-2017075381 A1 *  5/2017  ............. A61F 13/00

OTHER PUBLICATIONS

International Search report filed in PCT/US19/56430 dated Jan. 7, 2020.

*Primary Examiner* — Susan S Su
*Assistant Examiner* — Eric Rassavong
(74) *Attorney, Agent, or Firm* — Rankin, Hill & Clark LLP (57) ABSTRACT

A negative pressure device for applying to skin is configured to define a sealed enclosed three-dimensional space when at least a portion of the device is sealed against the skin. The device includes a body including at least one expandable segment that is configured to expand after the device has been sealed against the skin.

20 Claims, 7 Drawing Sheets

(56) References Cited

U.S. PATENT DOCUMENTS

| | | | |
|---|---|---|---|
| 8,535,283 B2* | 9/2013 | Heaton | A61M 1/0011 |
| | | | 604/319 |
| 10,046,095 B1 | 8/2018 | Middaugh | |
| 2008/0103462 A1 | 5/2008 | Wenzel | |
| 2009/0259203 A1 | 10/2009 | Hu | |
| 2010/0305524 A1 | 12/2010 | Vess | |
| 2012/0316538 A1* | 12/2012 | Heiser | A61M 1/90 |
| | | | 604/543 |
| 2014/0039423 A1* | 2/2014 | Riesinger | A61M 1/82 |
| | | | 604/315 |
| 2015/0202354 A1* | 7/2015 | Wall | A61L 15/60 |
| | | | 604/319 |

* cited by examiner

NEGATIVE PRESSURE DEVICE INCLUDING EXPANDABLE SEGMENT

BACKGROUND

Negative pressure is a term used to describe a pressure that is below normal atmospheric pressure. Known topical negative pressure devices range from cumbersome wrinkle reducing suction apparatuses to wound therapies that include fluid-permeable wound cavity filling elements, covering dressings, reasonably air-tight means for sealing against the skin, and drainage tubes connecting the wound site and cavity filling element to the vacuum source via a fluid collection canister.

To enable a more prolonged application of topical negative pressure, powered systems, which include a vacuum generation source such as a pump, have been developed and many examples of such systems are used today for skin treatments and restorative purposes like the temporary removal of wrinkles. Many of these systems, however, are not convenient for users. Such known systems can be large, heavy, noisy, uncomfortable, and not simple for users to apply and initiate a controlled pressure condition. Such known systems also rely on an outside power or vacuum source to create topical negative pressure conditions.

Such tissue treatment, surgery, and other advanced technical interventions are becoming more common given the occurrence of both the aging population, as well as increasingly compromised patient populations. This trend looks set to continue. In wound care, for example, healthcare professionals are now more likely to encounter wounds with complex healing problems that are difficult to manage. Attempts have been made to produce more simple mechanical devices able to apply topical and negative pressure to a tissue site. It will be appreciated that such a medical device, due to its relative simplicity of design, would be expected to reduce material costs and assembly costs. For example, attempts have been made to use a hand-pump system for the application of topical negative pressure at a tissue site. However, such a system fails to enable easier application by the user, discreet use, and prolonged convenient application of topical negative pressure, and, in fact, re-evacuation is often necessary. These can be serious deficiencies, particularly as many such systems are ideally useable for prolonged periods, such as overnight.

SUMMARY

In view of the foregoing, a negative pressure device for applying to skin is configured to define a sealed enclosed three-dimensional space when at least a portion of the device is sealed against the skin. The device includes a body including at least one expandable segment that is configured to expand after the device has been sealed against the skin.

DETAILED DESCRIPTION

Figure 1:
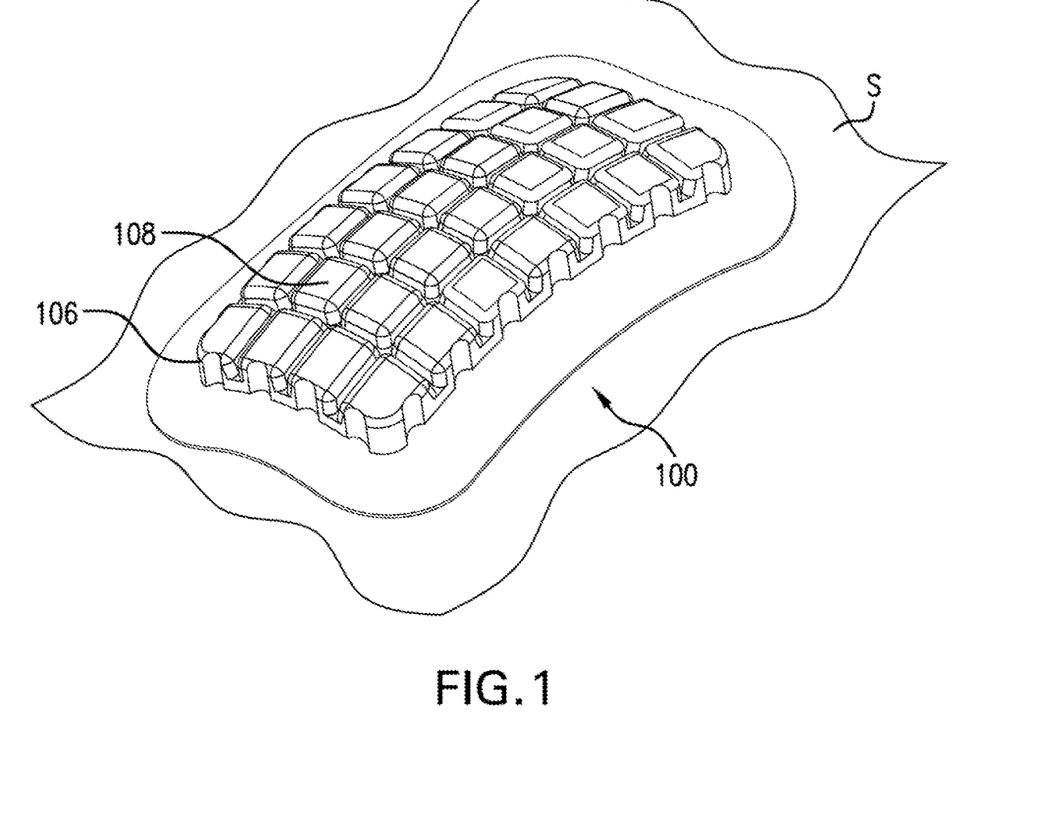
FIG. 1 is a schematic upper perspective view of a negative pressure affixed to skin.
Figure 2:
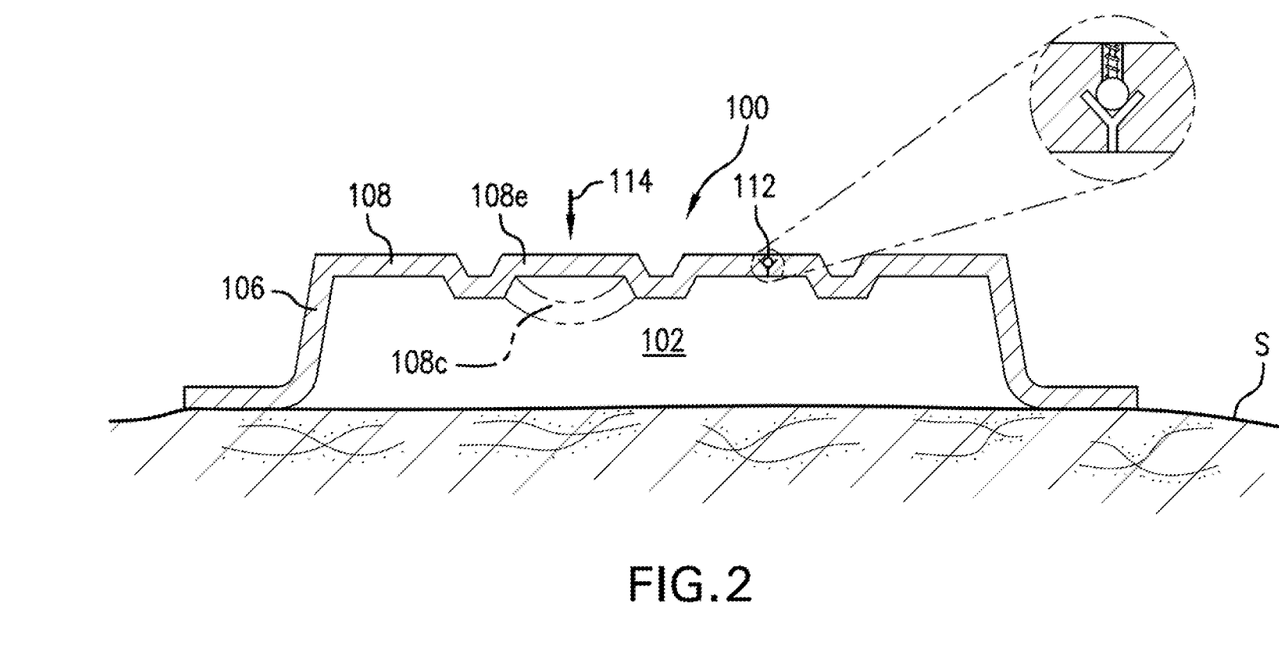
FIG. 2 is a schematic cross-sectional view of the negative pressure device including a pressure relief valve.

FIG. 1 depicts a negative pressure device 100 for applying to skin S. With reference to FIG. 2, the device 100 is configured to define a sealed enclosed three-dimensional space 102 when sealed against the skin S. Negative pressure, with relation to atmospheric pressure, can be achieved in the sealed enclosed three-dimensional space 102.

The negative pressure device 100 includes a body 106 including at least one expandable segment 108 that is configured to expand after the negative pressure device 100 has been sealed against the skin S. The negative pressure device 100 is shown including a plurality of expandable segments 108. Unless otherwise mentioned, if only one expandable segment 108 is being described, it is to be understood that each expandable segment 108 can be similarly constructed and operate in a similar manner.

In accordance with the ideal gas law, if the volume of the enclosed three-dimensional space 102 increases, then the gas pressure in the enclosed three-dimensional space 102 decreases when the same number of moles of gas is maintained in the enclosed three-dimensional space 102. Accordingly, if the expandable segment 108 is allowed to expand so as to increase the volume of the enclosed three-dimensional space 102, then the gas pressure within the enclosed three-dimensional space 102 decreases. As such, negative pressure (with respect to atmospheric pressure) can be applied to the skin S beneath the body 106 within the enclosed three-dimensional space 102.

FIG. 2 depicts the negative pressure device 100 including a pressure relief valve 112 on the body 106. The pressure relief valve 112 is configured to provide selective pneumatic communication between ambient and the sealed enclosed three-dimensional space 102. The pressure relief valve 112 is configured to open, thus providing communication between ambient and the sealed enclosed three-dimensional space 102, in response to a compressive force (depicted as arrow 114 in FIG. 2) exceeding atmospheric pressure being applied to the expandable segment 108. The pressure relief valve 112 is also configured to close, thus precluding communication between ambient and the sealed enclosed three-dimensional space 102, in response to the compressive force exceeding atmospheric pressure being removed from the expandable segment 108.

The expandable segments 108 are movable between a compressed state and an expanded state. When at least one of the expandable segments 108 is in the expanded state, which is depicted as expanded expandable segment 108e in FIG. 2, the volume of the sealed enclosed three-dimensional space 102 is greater than the volume of the sealed enclosed three-dimensional space 102 when the expandable segment 108 is in the compressed state, which is depicted in broken lines as compressed expandable segment 108c in FIG. 2. As seen in FIG. 2, the expandable segment 108 moves toward the skin S, which is shown in broken lines in FIG. 2, when the compressive force exceeding atmospheric pressure is applied to the expandable segment 108. The expandable segment 108 also moves away from the skin S when the compressive force exceeding atmospheric pressure is removed from the expandable segment 108, thus returning to the configuration shown in solid lines in FIG. 2.

The body 106 or the expandable segment 108 is constructed of a material with sufficient strength and resiliency to expand back toward the state shown in solid lines in FIG. 2 after 1-5 PSI of pressure above atmospheric pressure is applied to the expandable segment 108. The expandable segment 108 can be configured to move away from the skin S when pressure acting against an external surface of the body 106 is up to 20% greater than an internal pressure in the sealed enclosed three-dimensional space 102 beneath the body 106 acting against an internal surface of the body. When the expandable segment 108 is depressed to the configuration shown in broken lines in FIG. 2, the pressure relief valve 112 opens and air within the enclosed three-dimensional space 102 is allowed to exit to ambient. When the force is removed from the expandable segment 108, the pressure relief valve 112 closes. The expandable segment 108, however, is made from a material such that it overcomes the downward force (per the orientation shown in FIG. 2) of the partial vacuum within the sealed enclosed three-dimensional space 102 so as to return to the state shown in solid lines in FIG. 2. Since air has been expelled from the sealed enclosed three-dimensional space 102, fewer moles of air are present within the sealed enclosed three-dimensional space 102 and thus the gas pressure within the sealed enclosed three-dimensional space 102 is reduced as compared to prior to applying the force on the expandable segment 108.

Figure 3:
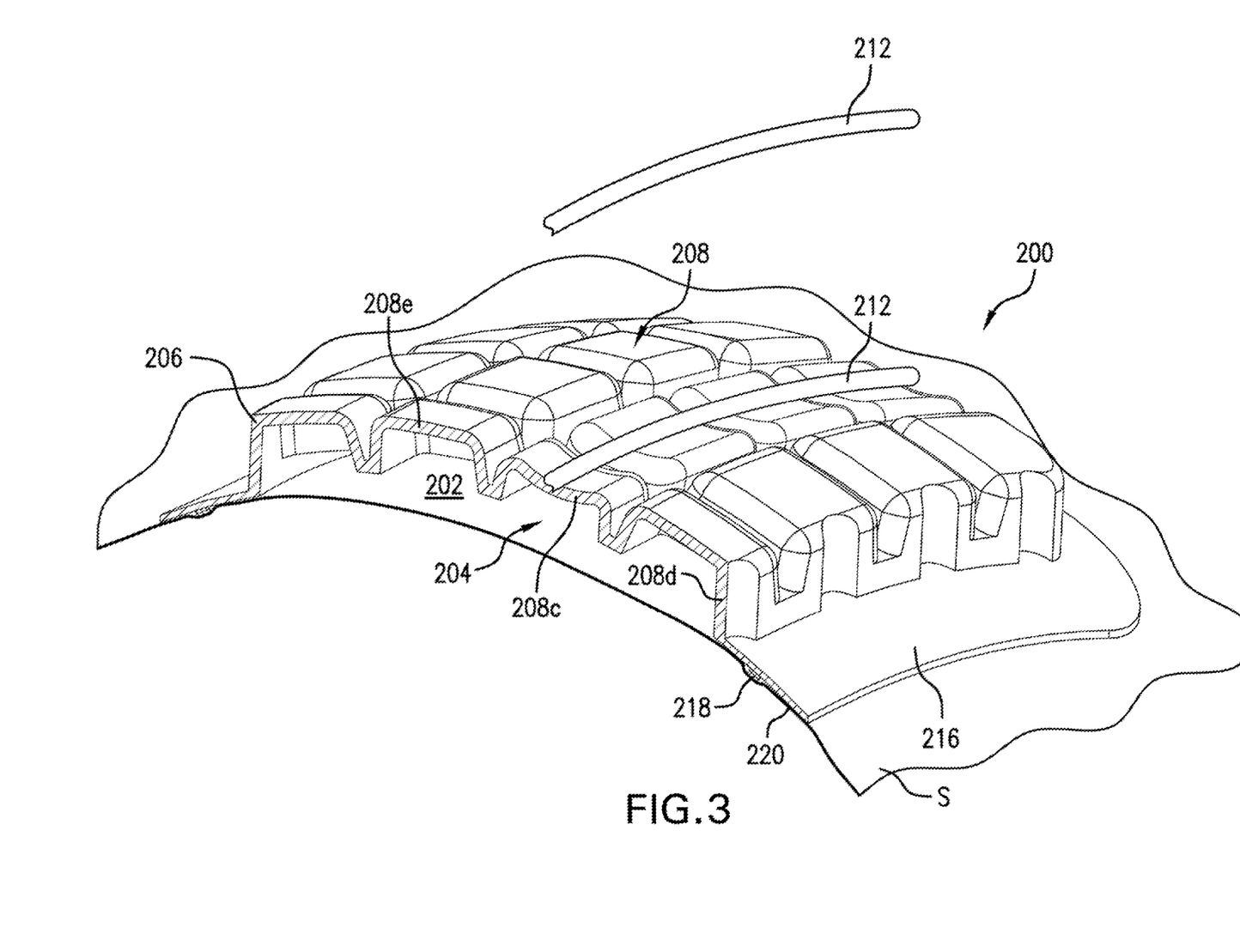
FIG. 3 is a schematic cross-sectional view of the negative pressure device including a retaining structure.

FIG. 3 depicts another embodiment of a negative pressure device 200 for applying to skin S. The negative pressure device 200 is configured to define a sealed enclosed three-dimensional space 202 when sealed against the skin S. The negative pressure device 200 includes a body 206 including at least one expandable segment (a plurality of expandable segments 208 is depicted). The expandable segments 208 are configured to expand after the negative pressure device 200 has been sealed against the skin S.

In the embodiment depicted in FIG. 3, the negative pressure device 200 further includes a retaining structure 212. As shown in FIG. 3, two retaining structures 212 are provided; however, a fewer or greater number of retaining structures 212 can be provided. Each retaining structure 212 connects with the body 206 or the expandable segments 208 such that the expandable segments 208 are compressed prior to removal of the retaining structure 212 from the body 206 or the expandable segments 208 to which the retaining structure 212 is connected. The retaining structure 212 can connect with the body 206 or the expandable segments 208 using an adhesive (not shown) or through a mechanical connection. The retaining structures 212 are typically connected with the body 206 or the expandable segments 208 prior to the negative pressure device 200 being sealed against the skin S, and then are removed after the negative pressure device 200 is sealed against the skin S.

FIG. 3 shows one of the retaining structures 212 having been removed from the body 206 and another of the retaining structures 212 still connected with the body 206. The retaining structures 212 are selectively removable from the body 206 or the expandable segments 208. The expandable segments 208 are movable between the compressed state, which is shown for the expandable segments 208c to which the retaining structure 212 is still connected in FIG. 3, and the expanded state in which the expandable segments 208e having the retaining structure 212 removed is shown in FIG. 3. The expandable segments 208 are configured to move from the compressed state toward the expanded state after the retaining structure 212 is removed from the body 206 or the expandable segment 208.

The negative pressure device 200 is affixed to the skin S around an apron 216, which is provided around a periphery of the body. The apron 216 and the body 206 can be an integrally formed piece of material and the apron 216 is conformable to contours on the human body. A sealing element 218 is provided on the lower surface 220 of the apron 216 to define the sealed enclosed three-dimensional space 202 when the negative pressure device 200 is sealed against the skin S.

The expandable segments 208 are typically compressed by the retaining structure 212 when the negative pressure device 200 is affixed to the skin S. After the negative pressure device 200 is affixed to the skin S, one or all of the retaining structures 212 can be removed from the body 206 and the expandable segments 208. The body 206 and/or the expandable segments 208 are made from a material with sufficient resiliency to overcome any partial vacuum in the sealed enclosed three-dimensional space 202 so as to expand from the position of the compressed expandable segments 208c to the position of the expanded expandable segments 208e. The expansion of the expandable segments 208 results in the volume of the sealed enclosed three-dimensional space 202 increasing. Since the same number of moles of air (or other gas) is present in the sealed enclosed three-dimensional space 202, the gas pressure within the sealed enclosed three-dimensional space 202 reduces below that of atmospheric pressure. The pressure applied by each retaining structure 212 on each expandable segment 208 can be about 3 PSI above atmospheric pressure. As such, as the expandable segments 208c move from the compressed state to the expanded state, which is shown by the expandable segments 208e, a reduction of 3 PSI within the sealed enclosed three-dimensional space 202 can occur, which can result in a relative negative vacuum within the sealed enclosed three-dimensional space 202 as compared to atmospheric pressure.

Figure 4:
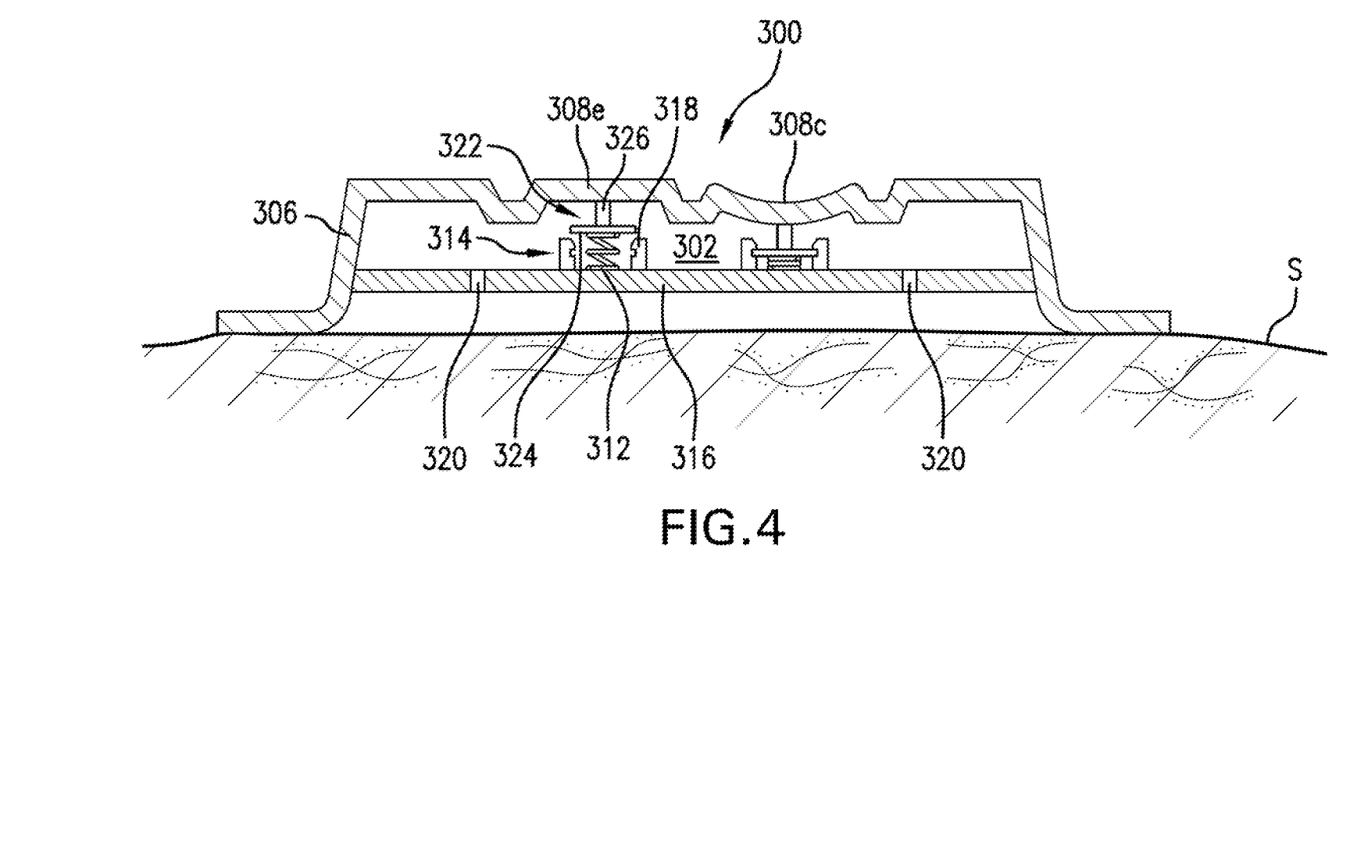
FIG. 4 is a schematic cross-sectional view of the negative pressure device including a biasing element.

FIG. 4 depicts another embodiment of a negative pressure device 300 for applying to skin S. The negative pressure device 300 is configured to define a sealed enclosed three-dimensional space 302 when sealed against the skin S. The device 300 includes a body 306 including at least one expandable segment 308 that is configured to expand after the device 300 has been sealed against the skin S.

FIG. 4 shows one of the expandable segments, i.e., an expanded expandable segment 308e, in an expanded state, and another of the expandable segments 308c, i.e., a compressed expandable segment 308c, in a compressed state. The negative pressure device 300 includes a biasing element, which is a spring 312 in the illustrated embodiment. The spring 312 connects with the body 306 or desired expandable segments 308 so as to bias the expandable segment 308 toward the expanded state.

The spring 312 can be part of a biasing assembly that includes a cam mechanism 314 that operates similarly to a conventional ball point pen mechanism. The cam mechanism 314 can mount to a support structure 316, which can include openings 320 to allow for a pneumatic communication between an upper surface of the support structure 316 and the lower surface of the support structure. A cam 318 can mount to the support structure 316. A follower 322 cooperates with the cam 318. The follower 322 can include a base 324 and a stem 326 that connects the base 324 with the expandable segment 308. The cam mechanism 314 associated with the spring 312 has a first state, which is shown for the cam mechanism 314 associated with the expanded expandable segment 308e, and a second state, which is shown for the cam mechanism 314 associated with the compressed expandable segment 308c.

When the negative pressure device 300 is applied to the skin S, each of the expandable segments 308 can be in the compressed state. An operator can then apply a force (downward per the orientation shown in FIG. 4) on each respective compressed expandable segment 308c, which will result in the follower 322 cooperating with the cam 318 in a manner such that the spring 312 acting against the support structure 316 urges the follower 322 upward (per the orientation shown in FIG. 4) such that the compressed expandable segment 308c moves toward the expanded state, which is shown as the expandable segment 308e. By allowing the expandable segments 308 to move from the compressed state toward the expanded state, the volume of the sealed enclosed three-dimensional space 302 is increased, which can result in a reduction in gas pressure within the sealed enclosed three-dimensional space 302.

FIG. 4 depicts the spring 312 biasing each expandable segment 308 away from the skin S after the negative pressure device 300 has been sealed against the skin S. In an alternative arrangement, the biasing direction of the spring 312 can be changed. For example, the spring 312 could be reconfigured to urge the expandable segment in a direction generally parallel with the skin S or in directions other than away from the skin S.

Figure 5:
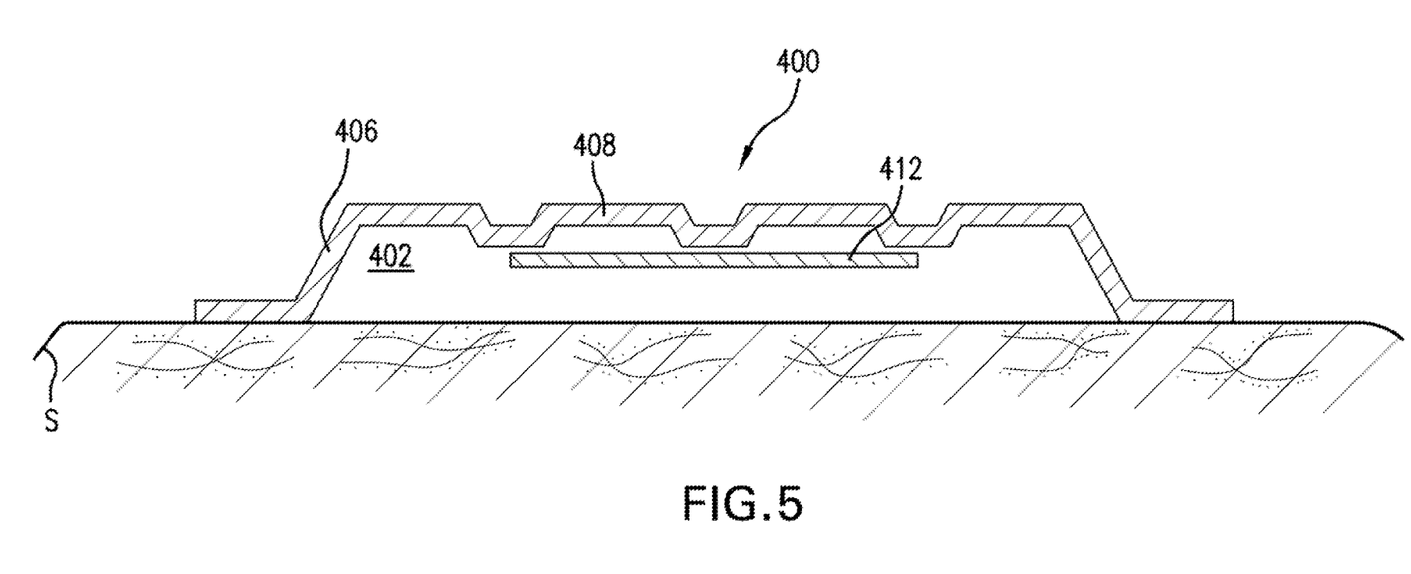
FIG. 5 is a schematic cross-sectional view of the negative pressure device including a reactor.

FIG. 5 depicts another embodiment of a negative pressure device 400 for applying to skin S. The negative pressure device 400 is configured to define a sealed enclosed three-dimensional space 402 when sealed against the skin S. Similar to the embodiments described above, the negative pressure device 400 includes a body 406 and at least one expandable segment 408 that is configured to expand after the negative pressure device 400 has been sealed against the skin S. The expandable segments 408 in FIG. 5 can be similar to the expandable segments 108, 208 and 308 described in FIGS. 1-4.

The negative pressure device 400 can further include a pump for removing gas from the sealed enclosed three-dimensional space 402. In FIG. 5, the pump is in the form of a reactor 412 that is configured to remove a selected gas from air. An example of such a reactor is described in US 2014/0109890 A1, which describes an oxygen based heater. The oxygen based heater, however, can be used as the reactor to consume oxygen within the sealed enclosed three-dimensional space 402 thus producing a partial vacuum within the sealed enclosed three-dimensional space 402 (i.e., a negative pressure condition). The reactor 412 may also be any combination of electro-chemical pumps, vacuum-on-demand devices (referred to herein as VOD), electrolyzers, pressure-reducing solid state devices, oxygen absorbing iron packets, getters of zirconium titanium, vanadium iron, lithium, lithium metal, magnesium, calcium, lithium barium combinations, zinc-air batteries, or other materials reactive with selective gases, for example, nitrogen, carbon dioxide, and oxygen gases found in air. Accordingly, the reactor 412 can be configured to consume oxygen, or the reactor can be configured to consume at least one non-inert gas.

Figure 6:
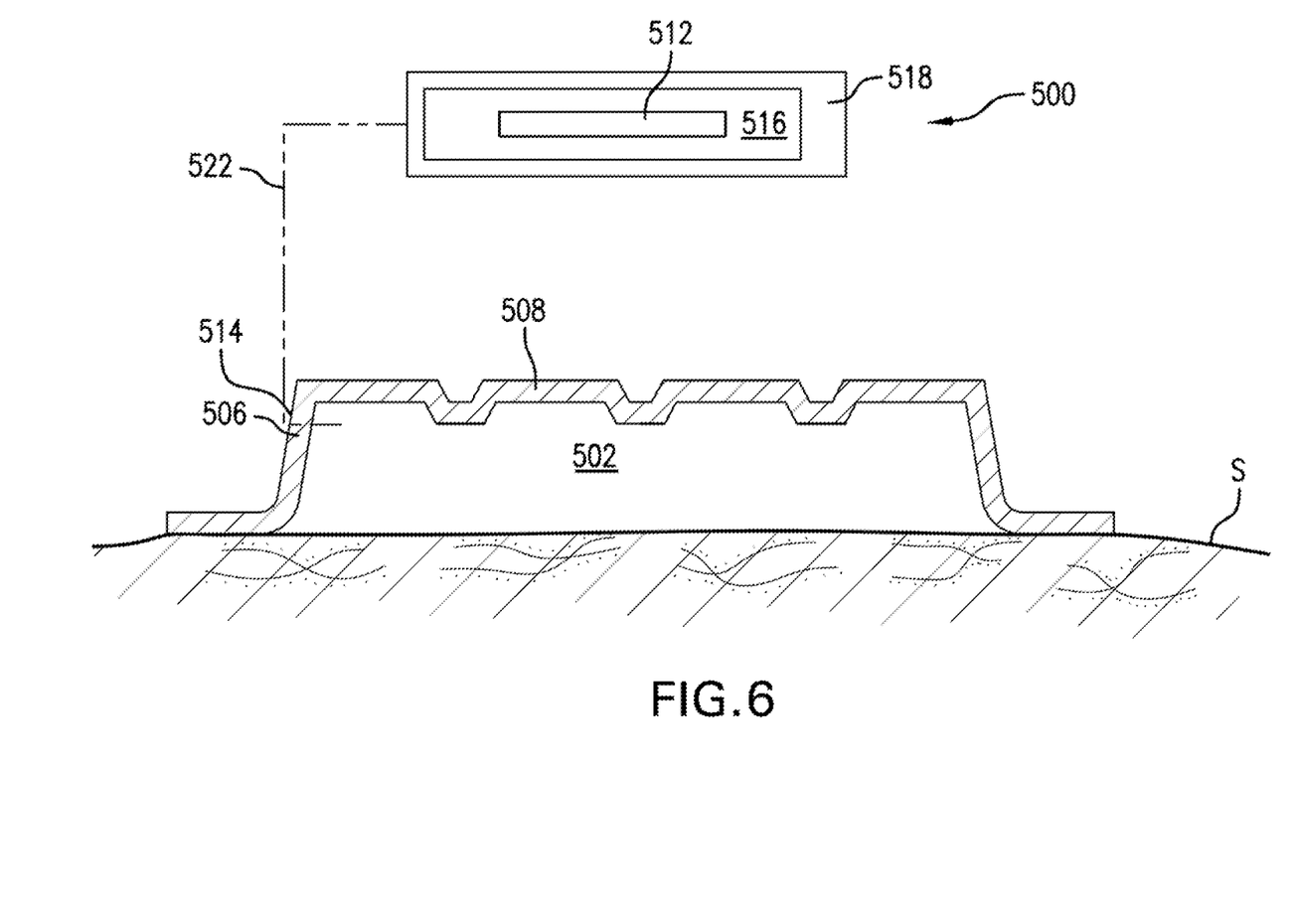
FIG. 6 is a schematic cross-sectional view of an alternative negative pressure device including the reactor.

FIG. 5 depicts the reactor 412 disposed within the sealed enclosed three-dimensional space 402 beneath the body 406. FIG. 6 depicts and embodiment of a negative pressure device 500 similar in all respects to the negative pressure device 400 shown in FIG. 5, however, a reactor 512, similar in all aspects to the reactor 412 described above, is instead in pneumatic communication with the sealed enclosed three-dimensional space 502 via an opening 514 in the body 506.

The reactor 512 can be disposed within a chamber 516 defined by a rigid container body 518. The chamber 516 can be configured to maintain a pre-defined chamber volume, which can remain constant or a minimum predetermined volume, while the gas is being consumed from the enclosed three-dimensional space 502 by the reactor 512. A pneumatic line 522 connects the chamber 516 to the sealed enclosed three-dimensional space 502. The body 506 can include at least one expandable segment 508 that is configured to expand after the device 500, and more particularly the body 506, has been sealed against the skin S.

For the embodiments depicted in FIGS. 5 and 6 only one reactor 412, 512 is depicted. If desired, multiple reactors 412, 512 can be provided with each respective negative pressure device 400, 500. The reactors 412, 512 can be designed to operate at different scavenging speeds. When two or more reactors 412, 512 are provided, one reactor 412, 512 can be designed to pump down the gas pressure in the enclosed three-dimensional space 402, 502 quickly, e.g., less than two minutes. A second (or other) reactor 412, 512 can be activated at the same time, however, the second (or other) reactor 412, 512 works more slowly. The slower working reactor 412, 512 can designed to reduce the oxidation coating covering the reactor 412, 512 allowing it work more effectively in low oxygen concentration. Where the reactor 412, 512 is a VOD, the VOD can also be used to further pump down the enclosed three-dimensional space 402, 502 to a therapeutic range if the oxygen level in the enclosed three-dimensional space 402, 502 is depleted, working to remove other gases in the enclosed three-dimensional space 402, 502, primarily nitrogen.

Figure 7:
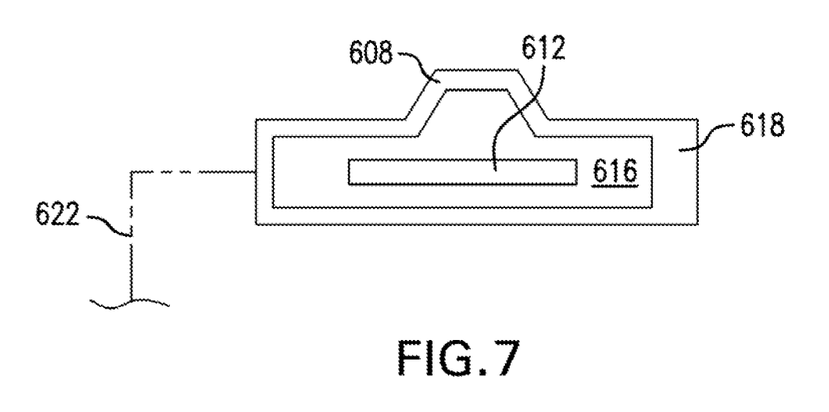
FIG. 7 is a schematic cross-sectional view of a reactor in a chamber of a container body having an expandable segment.

FIG. 7 depicts a reactor 612 disposed within a chamber 616 defined by a container body 618. The chamber 616 can be configured to maintain a pre-defined chamber volume while the gas is being consumed from a sealed enclosed three-dimensional space, which can be the enclosed three-dimensional spaces 102, 202, 302, 302, 502 mentioned above, or a sealed enclosed three-dimensional space underneath a bandage drape, for example for the wound therapy devices described in WO 2017/075381 A1 or the controlled pressure devices described in WO 2017/075331 A1. The container body 618 can include at least one expandable segment 608 that can be configured to operate in the same manner as the expandable segments 108, 208, 308, 408, 508. The chamber 616 can be connected for pneumatic communication with the enclosed three-dimensional spaces 102, 202, 302, 302, 502 mentioned above, the enclosed three-dimensional for the wound therapy devices described in WO 2017/075381 A1 or the enclosed three-dimensional for the controlled pressure devices described in WO 2017/075331 A1 via a fluid line 622, which is schematically depicted in FIG. 7. The expandable segment 608 can expand, thus increasing the volume of the chamber 616, after the device, which defines the aforementioned sealed enclosed three-dimensional space, has been sealed against the skin S.

The enclosed three-dimensional spaces 102, 202, 302, 302, 502 include an air volume portion occupied by air trapped in the respective enclosed three-dimensional space. In the case of a therapeutic negative pressure system, utilized for wound care, the range of reported operating pressures, relative to standard atmospheric pressure of 760 mmHg, are from −60 mmHg to −200 mmHg (absolute pressures of 560 to 700 mmHg). When using a reactor 512, 612 configured to consume oxygen, after all of the molecules of oxygen have been consumed by the reactor from the air in the overall system volume, the gas pressure in the overall system volume is reduced by 21% (or 159.6 mmHg)

assuming that the overall system volume was to remain constant. Thus, with the ideal case delivering maximum potential of −159.6 mmHg with dry air (note that the presence of humidity can change this number), designing a system to deliver the correct operating pressure, accounting for changes in the volume of the enclosed three-dimensional spaces 102, 202, 302, 302, 502 and exudate entering any wicking material and displacing air, is a formidable task.

The negative pressure devices in FIGS. 6 and 7 accomplish this task by dividing the negative pressure system into two volumes: the trapped air in the enclosed three-dimensional spaces 102, 202, 302, 302, 502 (or under a bandage), which is referred to as V1, and the chamber volume of each chamber 516, 616, which is referred to as V2. For example, if the chamber 616 is connected with a bandage, the bandage is flexible and absorbs fluid (exudate) as necessary. By absorbing fluid (exudate) only in the bandage, one can minimize the effect of volume loss, and thus pressure loss, on the system. The materials that make up the bandage can be soft and compliant, and the chamber 616 includes more rigid components to reduce volume loss in the pump assembly so as to increase the likelihood that the pressure in the overall volume of the system stays in the therapeutic range. In view of the aforementioned, it is desirable to have the predefined chamber volume, i.e., V2, of the chambers 516, 616 to be at least six times as large as the initial air volume portion, i.e., V1, (prior to the reactor consuming oxygen in this example) of the enclosed three-dimensional spaces 102, 202, 302, 302, 502.

If desired, a pressure relief valve, similar to the pressure relief valve 112, can be provided on the container body 618 to provide selective pneumatic communication between ambient and the chamber 616. The expandable segment 608 can be compressed and retained by a retaining structure, which can be similar to the retaining structure 212 described above. Such a retaining structure can connect with the container body 618 and the expandable segment 608 and be removable therefrom to allow the expandable segment 608 to move from the compressed state to the expanded state. The expandable segment 608 can also cooperate with biasing element, and operate similarly to the biasing assembly described above with reference to FIG. 4.

For each of the embodiments discussed above, a thin top covering or coating can be applied on the outer surface of the body 106, 206, 306, 406, 506 to provide a soft to touch feeling for the user. For each embodiment, the body 106, 206, 306, 406, 506 and the expandable segments 108, 208, 308, 408, 508 can be made of a resilient material and can be connected or co-molded, cast, formed or printed with a soft pliable material to add flexibility and form to body contours.

Embodiments of negative pressure devices have been described above in particularity. Modifications and alterations will occur to those upon reading and understanding the preceding detailed description. Moreover, elements from one embodiment, e.g., the retaining structures 212 in FIG. 3, can be employed in other embodiments, e.g., used with the negative pressure device 300 shown in FIG. 4. The invention is not limited only to the embodiments described above. Instead, the invention is broadly defined by the appended claims and the equivalents thereof. It will be appreciated that various aspects of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A negative pressure device for applying to skin, the device being configured to define a sealed enclosed three-dimensional space when at least a portion of the device is sealed against the skin, the device comprising:
   a body including at least one expandable segment that is configured to expand after the device has been sealed against the skin, wherein the at least one expandable segment includes a plurality of expandable segments; and
   a retaining structure connected with at least one of the body and the at least one expandable segment, wherein the retaining structure cooperates with the at least one expandable segment such that the at least one expandable segment is compressed prior to removal of the retaining structure from the body or the at least one expandable segment to which the retaining structure is connected, and prior to the device being sealed against the skin.

2. The negative pressure device of claim 1, further comprising a pressure relief valve on the body configured to provide selective pneumatic communication between ambient and the sealed enclosed three-dimensional space, wherein the pressure relief valve is configured to open in response to a compressive force exceeding atmospheric pressure being applied to the at least one expandable segment and is configured to close in response to the compressive force exceeding atmospheric pressure being removed from the at least one expandable segment.

3. The negative pressure device of any of claim 1, wherein the at least one expandable segment moves toward the skin when a compressive force exceeding atmospheric pressure is applied to the at least one expandable segment and the at least one expandable segment moves away from the skin when the compressive force exceeding atmospheric pressure is removed from the at least one expandable segment.

4. The negative pressure device of claim 1, wherein the retaining structure is selectively removable from at least one of the body and the at least one expandable segment, wherein the at least one expandable segment is configured to move away from the skin after the retaining structure is removed from at least one of the body and the at least one expandable segment.

5. A negative pressure device for applying to skin, the device being configured to define a sealed enclosed three-dimensional space when at least a portion of the device is sealed against the skin, the device comprising a body including at least one expandable segment that is configured to expand after the device has been sealed against the skin, wherein the at least one expandable segment includes a plurality of expandable segments, the negative pressure device further comprising a plurality of retaining structures each connected with at least one of the body and at least one expandable segment of the plurality of expandable segments.

6. A negative pressure device for applying to skin, the device being configured to define a sealed enclosed three-dimensional space when at least a portion of the device is sealed against the skin, the device comprising:
   a body including at least one expandable segment that is configured to expand after the device has been sealed against the skin;
   a biasing element connected with at least one of the body and the at least one expandable segment, wherein the biasing element cooperates with the at least one expandable segment so as to bias the at least one expandable segment toward an expanded state; and a cam mechanism including a cam and a follower configured to cooperate with the cam, wherein the follower is connected with the at least one of the body and the at least one expandable segment, and the biasing element acts on the follower to bias the at least one expandable segment toward the expanded state.

7. The negative pressure device of claim 6, wherein the biasing element cooperates with the at least one expandable segment so as to bias the at least one expandable segment away from the skin after the device has been sealed against the skin.

8. The negative pressure device of claim 6, when in the first state the biasing element biases the at least one expandable segment toward the expanded state, and when in the second state the biasing element biases the at least one expandable segment away from the skin.

9. The negative pressure device of claim 1, wherein the at least one expandable segment is configured to move toward an expanded state when pressure acting against an external surface of the expandable segment is up to 20% greater than an internal pressure in the sealed enclosed three-dimensional space acting against an internal surface of the expandable segment.

10. The negative pressure device of claim 1, wherein the body is made from a flexible material and includes an apron conformable to contours of a human body.

11. The negative pressure device of claim 1, further comprising a reactor configured to consume oxygen or at least one non-inert gas.

12. The negative pressure device of claim 11, wherein the reactor is disposed in the sealed enclosed three-dimensional space beneath the body.

13. The negative pressure device of claim 1, further comprising a chamber in fluid communication with the sealed enclosed three-dimensional space via an opening in the body and a reactor configured to consume oxygen or at least one non-inert gas, the chamber configured to maintain a predefined chamber volume while the gas is being consumed from the enclosed three-dimensional space.

14. The negative pressure device of claim 13, wherein the reactor is in fluid communication with the chamber.

15. The negative pressure device of claim 13, wherein the reactor is disposed in the chamber.

16. The negative pressure device of claim 15, further comprising a container body in fluid communication with the sealed enclosed three-dimensional space and defining the chamber, the container body including the at least one expandable segment.

17. The negative pressure device of claim 16, wherein the reactor is disposed in the chamber.

18. The negative pressure device of claim 16, wherein the sealed enclosed three-dimensional space includes an initial air volume portion occupied by air trapped in the sealed enclosed three-dimensional space prior to the reactor consuming the gas, wherein the predefined chamber volume is at least six times larger than the initial air volume portion.

19. The negative pressure device of claim 6, wherein the cam mechanism has a first state associated with the expanded state of the at least one expandable segment, and a second state associated with a compressed state of the at least one expandable segment, and wherein when the cam mechanism is in the second state, and the follower is pressed toward the skin, the follower cooperates with the cam such that the spring acts against the follower toward the second state such that the at least one expandable element moves toward the expanded state.

20. The negative pressure device of claim 6, further comprising a support structure disposed in the body and configured to allow pneumatic communication between an upper surface of the support structure and a lower surface of the support structure, wherein the cam is mounted on the support structure and configured to cooperate with the follower such that the biasing member acting against the support structure urges the follower away from the skin and moves the expandable segment toward the expanded state.

* * * * *